United States Patent
Mi et al.

(10) Patent No.: US 9,828,579 B2
(45) Date of Patent: Nov. 28, 2017

(54) CELL CULTURE APPARATUS AND METHOD OF USING THE SAME

(71) Applicant: DrSignal BioTechnology co., Ltd, New Taipei (TW)

(72) Inventors: Hsin-Wu Mi, New Taipei (TW); Ming-Cheng Lee, New Taipei (TW)

(73) Assignee: DrSignal BioTechnology co., Ltd, New Taipei (TW)

( * ) Notice: Subject to any disclaimer, the term of this patent is extended or adjusted under 35 U.S.C. 154(b) by 391 days.

(21) Appl. No.: 14/686,661

(22) Filed: Apr. 14, 2015

(65) Prior Publication Data

US 2015/0299642 A1 Oct. 22, 2015

Related U.S. Application Data

(60) Provisional application No. 61/981,362, filed on Apr. 18, 2014.

(51) Int. Cl.
| | |
|---|---|
| *C12M 1/00* | (2006.01) |
| *C12M 1/34* | (2006.01) |
| *C12M 3/00* | (2006.01) |
| *C12M 1/36* | (2006.01) |
| *C12M 1/12* | (2006.01) |

(52) U.S. Cl.
CPC ............ *C12M 41/48* (2013.01); *C12M 23/48* (2013.01); *C12M 23/50* (2013.01); *C12M 29/00* (2013.01); *C12M 31/10* (2013.01); *C12M 37/00* (2013.01); *C12M 41/46* (2013.01)

(58) Field of Classification Search
CPC ...... C12M 23/48; C12M 23/50; C12M 29/00; C12M 31/10; C12M 37/00; C12M 41/46; C12M 41/48

See application file for complete search history.

(56) References Cited

U.S. PATENT DOCUMENTS

| | | | |
|---|---|---|---|
| 2003/0040104 A1* | 2/2003 | Barbera-Guillem | ... C12M 23/24 435/286.2 |
| 2008/0090288 A1* | 4/2008 | Hibino | ................... C12M 23/50 435/307.1 |

* cited by examiner

*Primary Examiner* — Nathan Bowers
*Assistant Examiner* — Lydia Edwards
(74) *Attorney, Agent, or Firm* — patenttm.us (57) ABSTRACT

A cell culture apparatus comprises at least one storage space, at least one barrier, a working space, a sterilization space, and a control space. The at least one storage space comprises a container shelf, an upright track, a rotatable holder, and a light tube. The working space comprises a filling station and an inspecting station. The filling station comprises a first delivering device, an open-close device, and a filling mechanism. The inspecting station comprises a first inspecting mechanism and a second delivering device. Also provided is a method of using the cell culture apparatus including steps of filling, inspecting, or collecting cell cultures, therefore, the cell culture apparatus performs multiple cell culture processes automatically.

15 Claims, 7 Drawing Sheets

100
CELL CULTURE APPARATUS AND METHOD OF USING THE SAME

CROSS REFERENCE

This application claims priority to U.S. Provisional Patent Application Ser. No. 61/981,362, filed on Apr. 18, 2014, the content of which is hereby incorporated by reference in its entirety.

BACKGROUND OF THE INVENTION

1. Field of the Invention

The present invention relates to a cell culture apparatus, especially to a cell culture apparatus that automatically moves the containers between different work stations of the cell culture apparatus for multiple processes of cell culturing.

2. Description of the Prior Arts

The cell culture technique is well developed in the contemporary time. The cultured cells are used in different fields such that massive production of the cultured cells is urgently needed. Because cell culture involves multiple processes, multiple technicians are hired to move the containers with the culture media therein between different work stations to perform different processes. However, the labor-intensive aspect costs much money and lacks efficiency.

Currently automatic culture apparatuses following manual culture operations using articulated robot manipulators are mainly developed. For example, U.S. Pat. No. 8,883,492 provides a space-saving cell culture apparatus providing a short distance between the instruments comprising a cell culture chamber, a refrigerator, a control unit, and an intermediate chamber. However, when the cells are culturing, devices are left idle, and once any part of the chamber is contaminated, all of the apparatus need to be shut down and cultured cells must be abandoned.

SUMMARY OF THE INVENTION

To overcome the shortcomings of the conventional cell culture apparatus, the present invention provides a cell culture apparatus comprising at least one storage space, at least one barrier, a working space, a sterilization space, and a control space. The at least one storage space comprises a container shelf, an upright track, a rotatable holder, and a light tube. The container shelf is mounted in the at least one storage space; the upright track is adjacent to the container shelf; the rotatable holder is rotatably and moveably connected to the upright track. Each of the at least one barrier, which is adjacent to the upright track of the at least one storage space, comprises a first gate. The working space has two opposite sides and comprises a filling station and an inspecting station. The filling station comprises a first delivering device, an open-close device, and a filling mechanism; the first delivering device has two opposite sides, and the first delivering device is moveably mounted in the working space with one of the sides of the first delivering device nearby the at least one barrier; the open-close device is mounted in the working space nearby the other side of the first delivering device; and the filling mechanism is adjacent to the open-close device and nearby the first delivering device. The inspecting station comprises a first inspecting mechanism and a second delivering device; the first inspecting mechanism is mounted in the working space, and the first inspecting mechanism is adjacent to the open-close device of the filling station; and the second delivering device is connected to the first inspecting mechanism.

Preferably, the at least one storage space further comprises a light tube mounted in the storage space. More preferably, the light tube is a Light-Emitting Diode (LED) light tube or a UV (ultraviolet) light tube.

Preferably, the working space further comprises a collecting station mounted beside the filling station.

Preferably, the second delivering device is a robotic arm.

Preferably, the inspecting station further comprises a second inspecting mechanism located between the first inspecting mechanism and the first delivering device.

Preferably, the cell culture apparatus further comprises a sterilization space and a control space, the sterilization space is connected to one of the sides of the working space, the other side of the working space is connected to the at least one barrier, and the control space is adjacent to the storage space and the working space.

More preferably, the sterilization space comprises a second gate and a UV sterilizer, the second gate is adjacent to the filling station of the working space, and the UV sterilizer is mounted in the sterilization space.

More preferably, the sterilization space is a laminar flow hood.

Preferably, the at least one storage space is three storage spaces which are adjacent to one another.

In one another aspect, the present invention also provides a method of using the above mentioned cell culture apparatus, comprising the following steps: setting multiple containers into the container shelf; capturing one of the containers by the rotatable holder; opening the first gate of the barrier when the rotatable holder holding the container is rotated and inserted into the first delivering device of the filling station of the working space; processing the container by at least one of the following processes: a filling process, an inspecting process, and a collecting process; after processing the at least one process, placing the container at the first delivering device, and opening a cap of the container by the open-close device; filing the container by the filling mechanism, and then closing the cap of the container by the open-close device; and moving the container by the rotatable holder back to the container shelf.

Preferably, the method further comprises replacing the storage space or increasing an amount of the storage space when the storage space is culturing cells.

Preferably, the at least one process is the filling process, the container is placed at the first delivering device, and the cap of the container is opened by the open-close device; the container is filled by the filling mechanism, and then the cap of the container is closed by the open-close device.

Preferably, the at least one process is the inspecting process, the container is placed at the first delivering device, and the second delivering device of the inspecting station delivers the container to the first inspecting mechanism.

More preferably, the method further comprises placing the container at the first delivering device, and delivering the container to the second inspecting mechanism and then to the first inspecting mechanism by the second delivering device of the inspecting station.

Preferably, the at least one process is the collecting process, the container is placed at the first delivering device, and the cap of the container is opened by the open-close device; the first delivering device pivots back and forth to pour medium from the container to the collecting station; the container is filled by the filling mechanism, and then the cap of the container is closed by the open-close device.

The main objective of the present invention is to provide a cell culture apparatus that performs multiple processes automatically. The cell culture apparatus as described has the following advantages:

1. The containers are moved between different processes automatically such that the cell culture apparatus as described saves manpower.

2. When the containers in the storage space are culturing cells, the storage space can be replaced or increased in amount, such that the working space can keep working rather than stay idle.

3. The barrier separates the storage space and the working space such that probability of contamination can be efficiently decreased.

4. The sterilization space is connected to the working space such that the disposable tubes or the contaminated devices in the working space can be rapidly delivered to the sterilization space for sterilization.

Other objectives, advantages and novel features of the invention will become more apparent from the following detailed description when taken in conjunction with the accompanying drawings.

DETAILED DESCRIPTION OF THE PREFERRED EMBODIMENTS

EXAMPLE 1

The Cell Culture Apparatus

Figure 1:
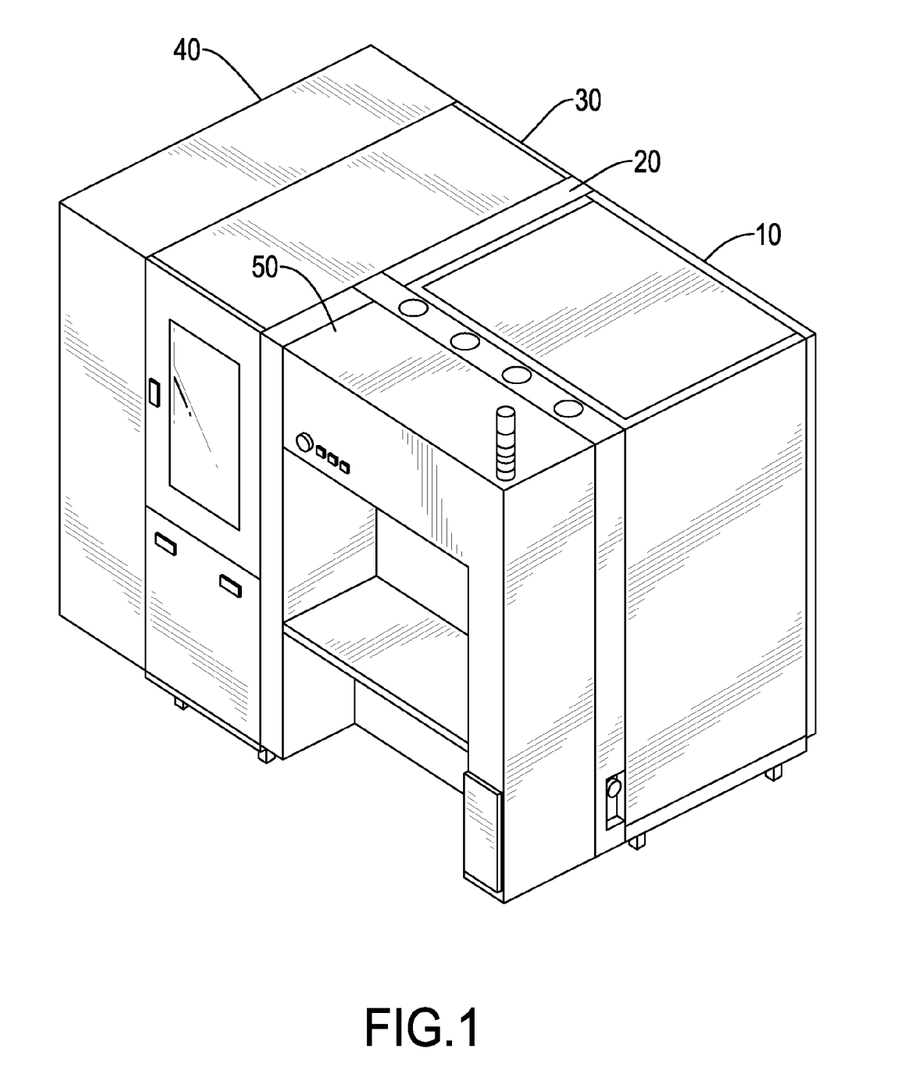
FIG. 1 is a perspective view of a cell culture apparatus of the present invention.
Figure 2:
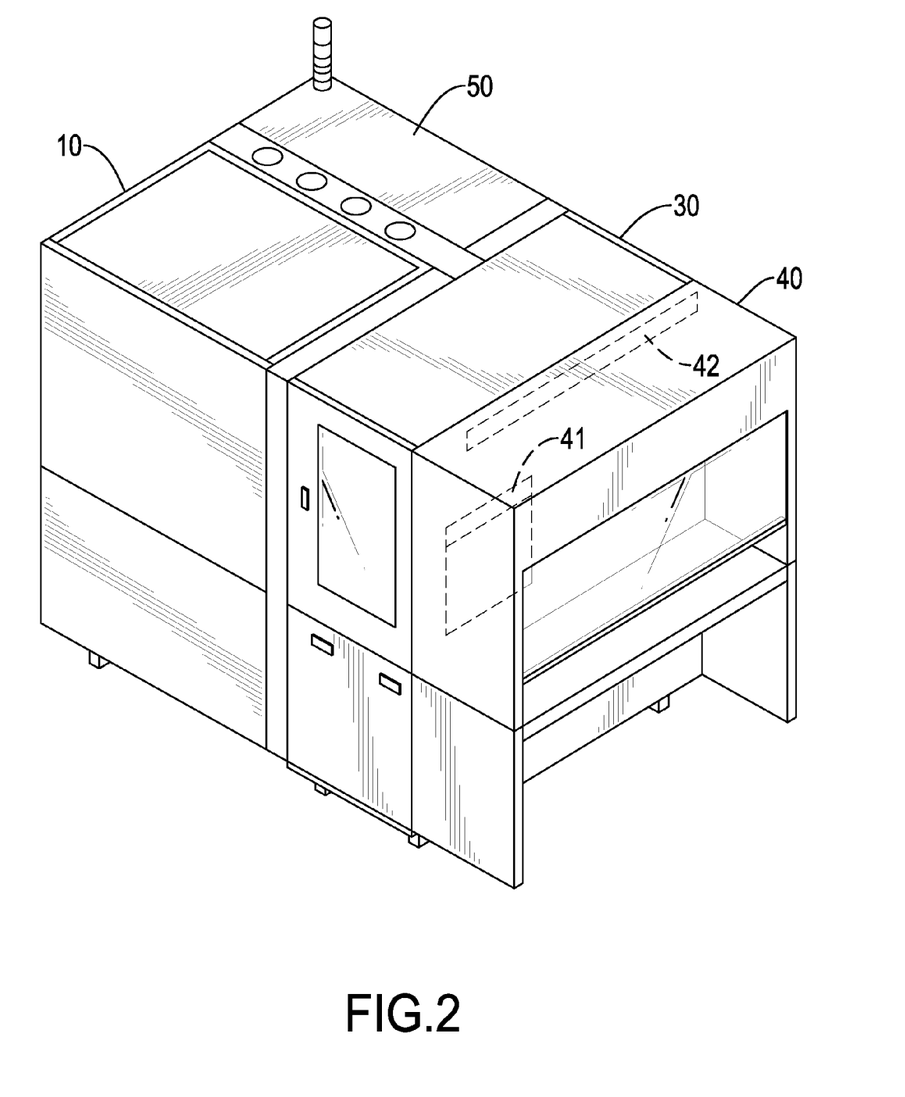
FIG. 2 is another perspective view of the cell culture apparatus of the present invention.

As shown in FIGS. 1 and 2, the present invention provides a cell culture apparatus, comprising a storage space 10, at least one barrier 20, a working space 30, a sterilization space 40, and a control space 50.

Figure 3:
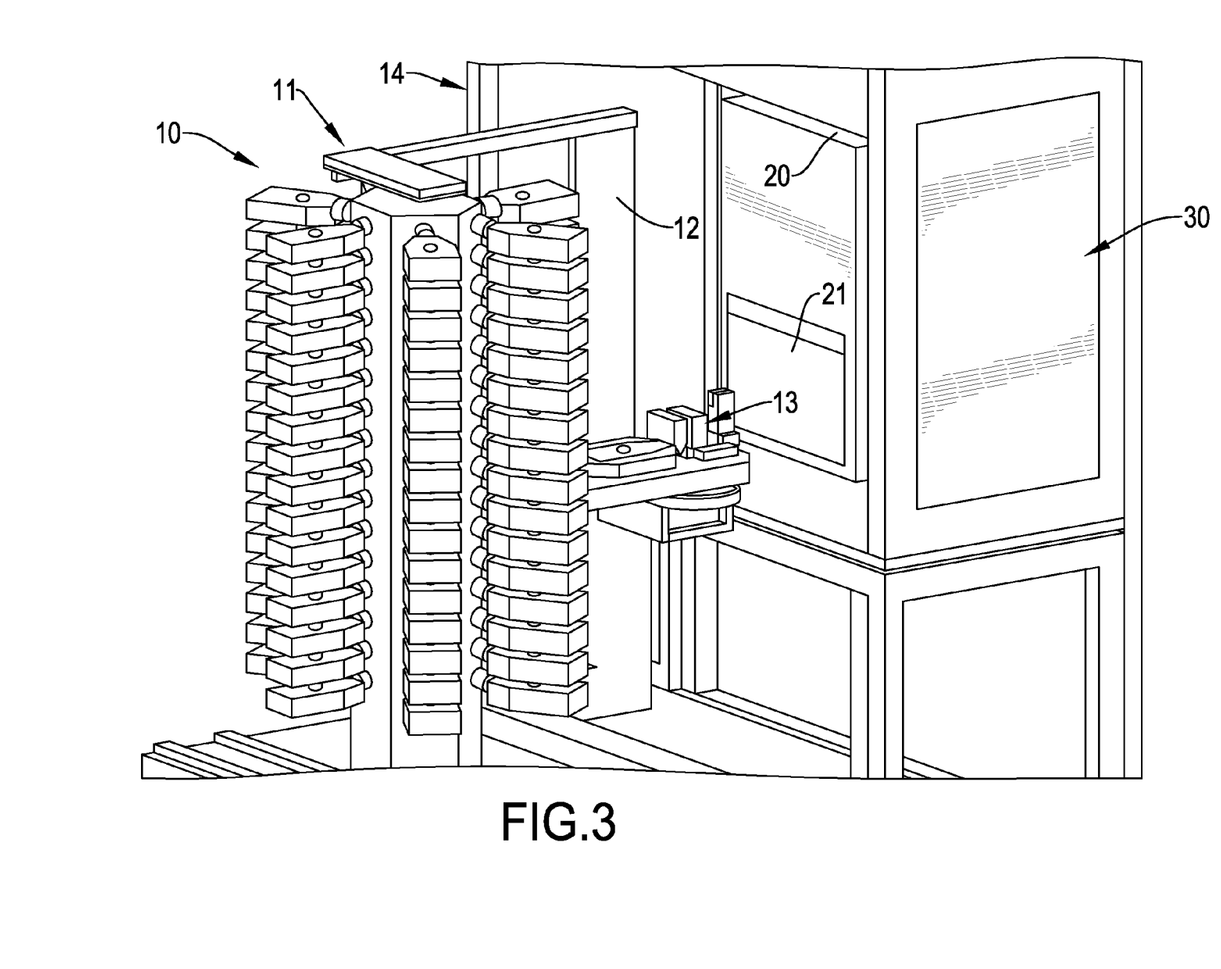
FIG. 3 is a perspective view of a storage space of the cell culture apparatus of the present invention.

As shown in FIGS. 1 to 3, the storage space 10 comprises a container shelf 11, an upright track 12, a rotatable holder 13, and a light tube 14. The container shelf 11 is mounted in the storage space 10; the upright track 12 is adjacent to the container shelf 11; the rotatable holder 13 is rotatably and moveably connected to the upright track 12; the light tube 14 is mounted in the storage space 10; in a preferred embodiment, the light tube 14 is a LED light tube or a UV light tube. When the containers in the storage space 10 are culturing cells, the storage space 10 can be replaced with another storage space 10, such that the storage space 10 is detachable and the working space 30 can keep working rather than stay idle.

The at least one barrier 20 is adjacent to the upright track 12 of the storage space 10, and the at least one barrier 20 is between the storage space 10 and the working space 30. The at least one barrier 20 comprises a first gate 21 which can allow the rotatable holder 13 to go into the working space 30.

Figure 4:
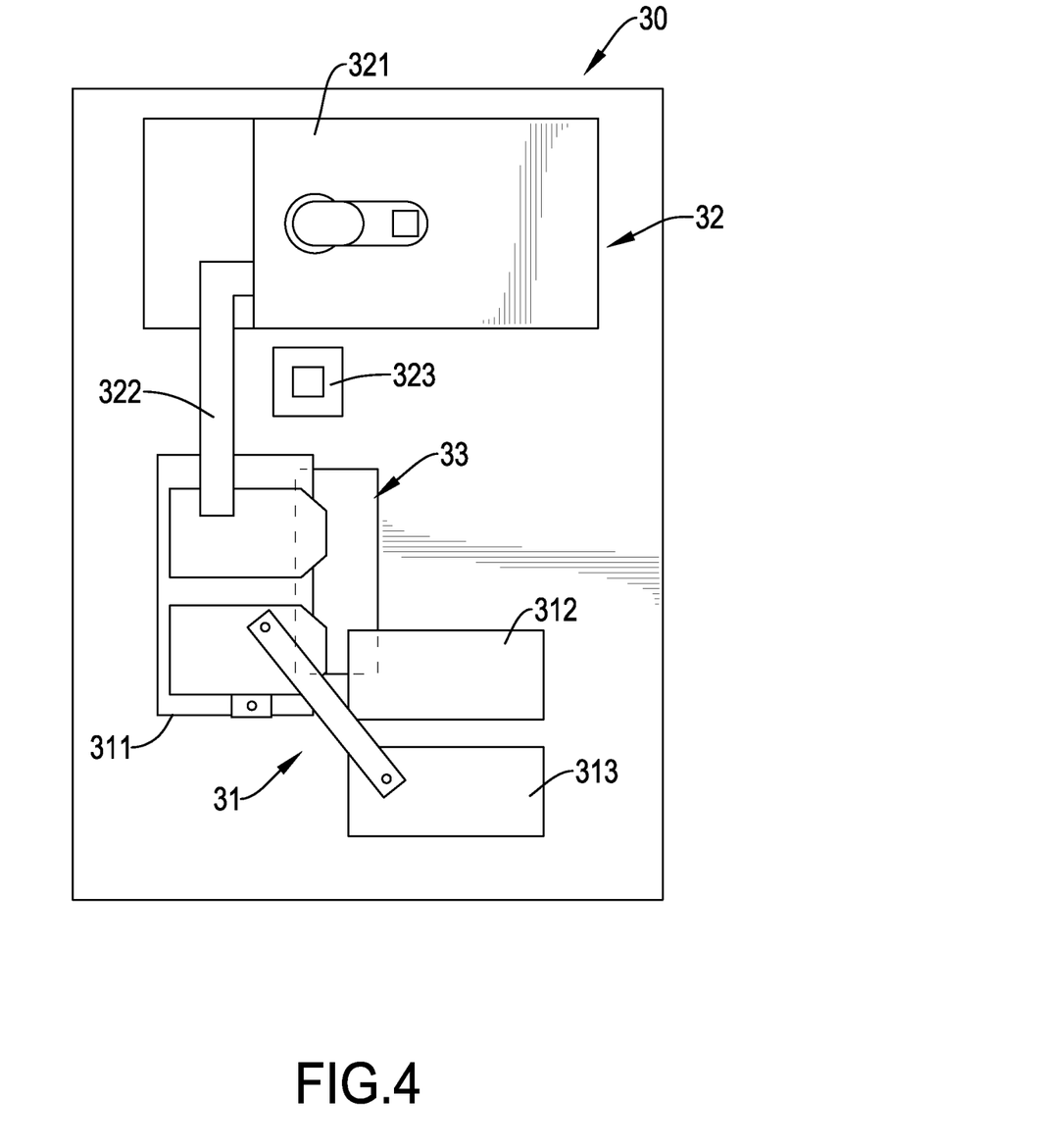
FIG. 4 is a top view of a working space of the cell culture apparatus of the present invention.
Figure 5:
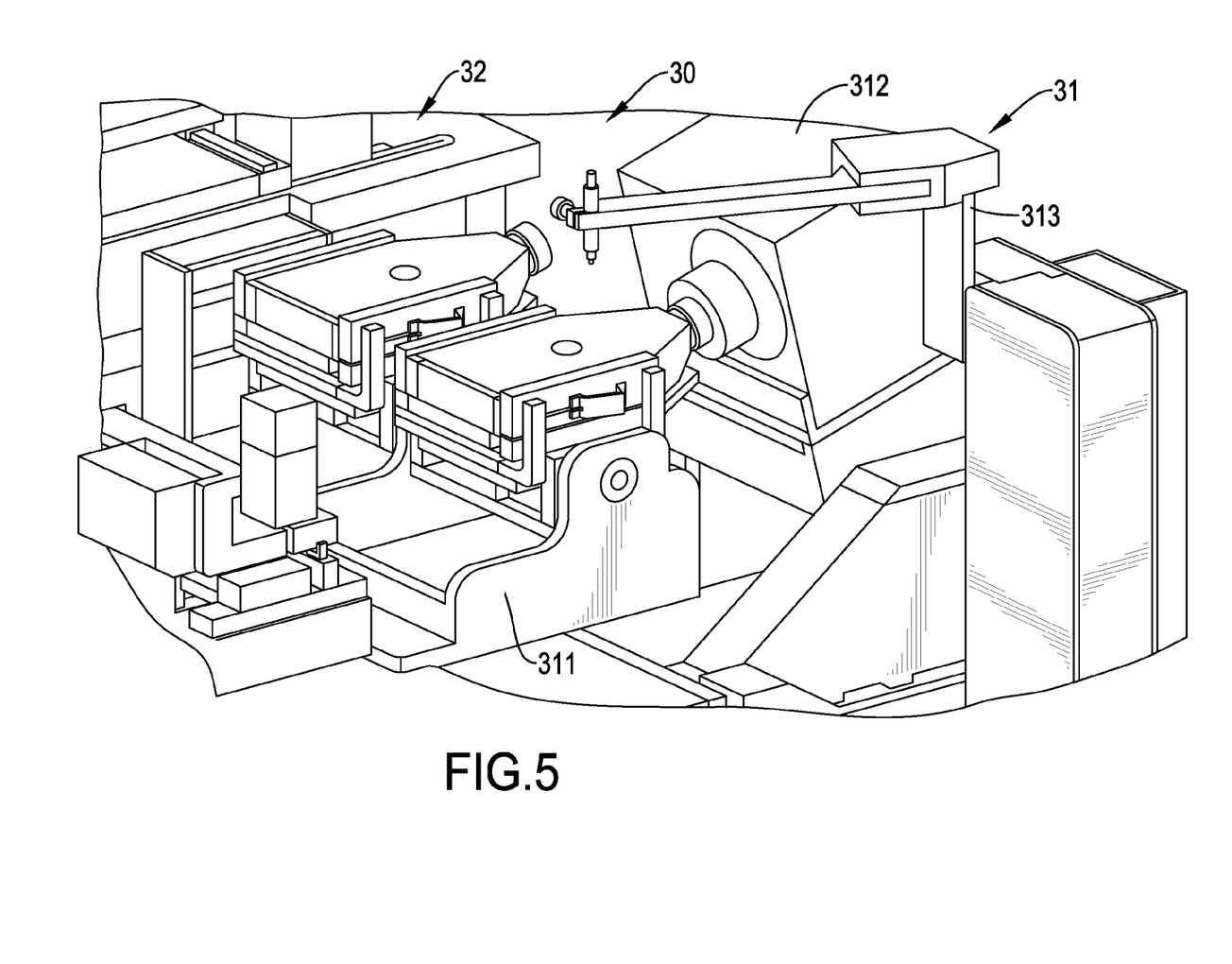
FIG. 5 is a perspective view of a filling station and a collecting station of the working space of the cell culture apparatus of the present invention.
Figure 6:
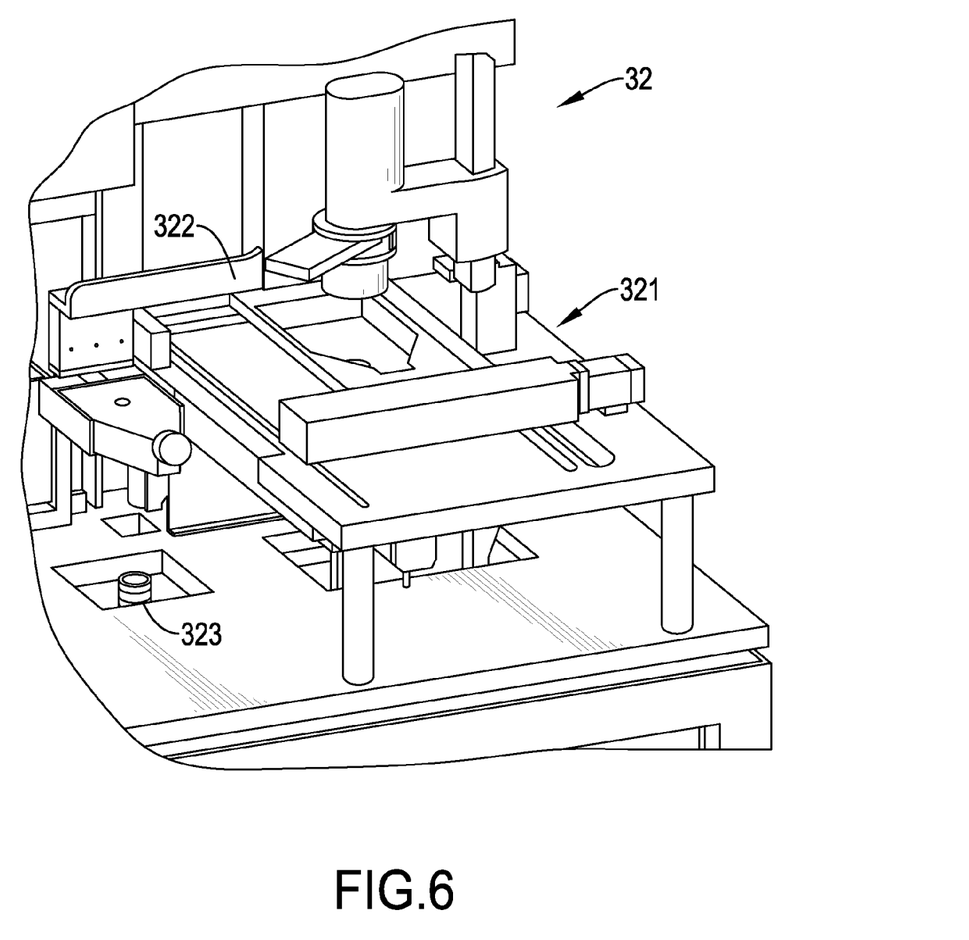
FIG. 6 is a perspective view of an inspecting station of the working space of the cell culture apparatus of the present invention.

As shown in FIGS. 3 to 5, the working space 30 has two opposite sides and comprises a filling station 31, an inspecting station 32, and a collecting station 33. The filling station 31 comprises a first delivering device 311, an open-close device 312, and a filling mechanism 313. The first delivering device 311 has two opposite sides, and the first delivering device 311 is moveably mounted in the working space 30 with one of the sides of the first delivering device 311 nearby the barrier 20; the open-close device 312 is mounted in the working space 30 and nearby the other side of the first delivering device 311; the filling mechanism 313 is adjacent to the open-close device 312 and nearby the first delivering device 311. As shown in FIGS. 5 to 6, the inspecting station 32 comprises a first inspecting mechanism 321, a second delivering device 322, and a second inspecting mechanism 323. The first inspecting mechanism 321 is mounted in the working space 30, and is adjacent to the first delivering device 311 of the filling station 31. In a preferred embodiment, the first inspecting mechanism 321 is a microscope which can observe whether the cells are contaminated or not. In a preferred embodiment, the first inspecting mechanism 321 can detect whether the cell types are normal or abnormal through comparison with the installed normal-cell-type images. The second delivering device 322 mounted in the first inspecting mechanism 321 can deliver a container between the first delivering device 311 and the first inspecting mechanism 321 back and forth. In a preferred embodiment, the second delivering device 322 is a robotic arm. The second inspecting mechanism 323 is located between the first inspecting mechanism 321 and the first delivering device 311. In a preferred embodiment, the second inspecting mechanism 323 is a cell observing mechanism as a camera function which can observe the cells condition in two to ten times magnification. As shown in FIG. 4, the collecting station 33 is mounted beside the filling station 31. In a preferred embodiment, the collecting station 33 is mounted below the filling station 31. The working space 30 is sealed by the barrier 20, as a result, when extra storage space(s) is/are added or when the storage space 10 is replaced by another storage space 10, the working space 30 can maintain a sterile status.

As shown in FIGS. 1 and 2, the sterilization space 40 is connected to one of the sides of the working space 30, and the other side of the working space 30 is connected to the barrier 20. The sterilization space 40 comprises a second gate 41 and a UV sterilizer 42. The second gate 41 is adjacent to the working space 30; the UV sterilizer 42 is mounted in the sterilization space 40. In a preferred embodiment, the sterilization space 40 is a laminar flow hood. The devices or mechanisms can be delivered from the working space 30 through the second gate 41 to the sterilization space 40.

The control space 50 is adjacent to the storage space 30 and the working space 10. The control space 50 includes a computer for analyzing data or transmitting images from the inspecting station 32, adjusting movement parameters of any device or mechanism and processing of filling, inspecting, and collecting.

Figure 7:
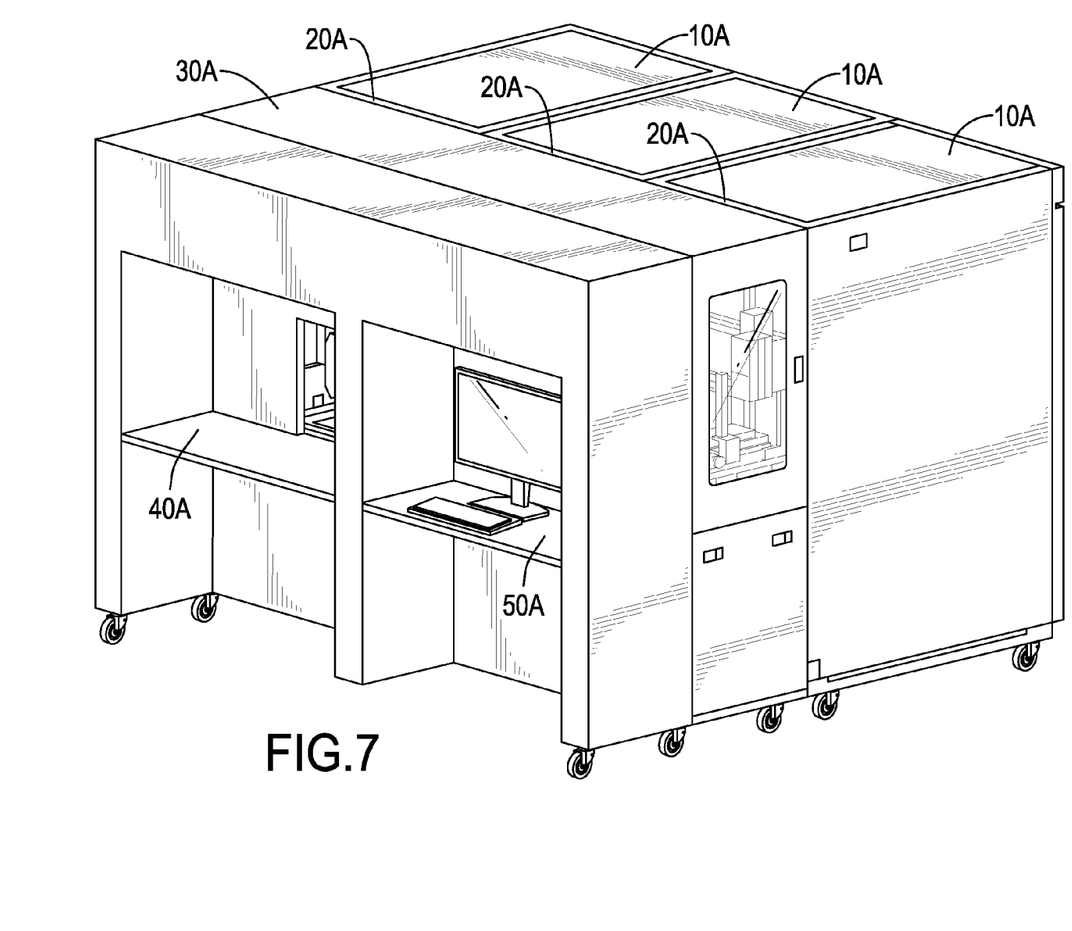
FIG. 7 is a perspective view of another cell culture apparatus of the present invention.

As shown in FIG. 7, the present invention also provides another cell culture apparatus, comprising three storage spaces 10A, three barriers 20A, a working space 30A, a sterilization space 40A, and a control space 50A. The three storage spaces 10A are adjacent to one another, and the three storage spaces 10A are also connected to the working space 30A via the barriers 20A. The barriers 20A are mounted between the storage spaces 10A and the working space 30A. The working space 30A has two opposite sides. The sterilization space 40A and the control space 50A are adjacent to each other, the sterilization space 40A and the control space 50A both connect to one of the sides of the working space 30A, and the other side of the working space 30A is connected to the barriers 20A or the storage spaces 10A. When the containers in the storage space are culturing cells, the storage space can be replaced or increased in amount.

EXAMPLE 2

The Steps of Filling Process

As shown in FIGS. 3 to 5, the filling process is mainly done in the filling station 31. Before filling, multiple containers are set into the container shelf 11, and one of the containers is caught by the rotatable holder 13. The first gate 21 of the barrier 20 is opened when the rotatable holder 13 holding the container is rotated and inserted into the first delivering device 311 of the filling station 31 of the working space 30. When filling, the container is placed at the first delivering device 311, and a cap of the container is opened by the open-close device 312. The container is filled by the filling mechanism 313, and then the cap of the container is closed by the open-close device 312. After filling, the container is caught by the rotatable holder 13 back to the container shelf 11.

EXAMPLE 3

The Steps of Inspecting Process

As shown in FIGS. 4 to 6, the inspecting process is mainly done in the inspecting station 32. Before inspecting, multiple containers are set into the container shelf 11, and one of the containers is caught by the rotatable holder 13. The first gate 21 of the barrier 20 is opened when the rotatable holder 13 holding the container is rotated and inserted into the first delivering device 311 of the filling station 31 of the working space 30. During inspection, the container is placed at the first delivering device 311, and the container is delivered by the second delivering device 322 of the inspecting station 32 to the second inspecting mechanism 323. The inside of the container is inspected by the second inspecting mechanism 323 to make sure that the cell culturing conditions in the container are available; then the container is delivered by the second delivering device 322 to the first inspecting mechanism 321. The inside of the container is inspected by the first inspecting mechanism 321 for counting the cell number and exploring whether the cell morphology is normal or abnormal. After the inspection, the container is delivered by the second delivering device 322 back to the first delivering device 311, and the container is caught by the rotatable holder 13 back to the container shelf 11.

EXAMPLE 4

The Steps of Collecting Process

As shown in FIGS. 3 to 5, the collecting process is mainly done in the collecting station 33. Before the collecting, multiple containers are set into the container shelf 11, and one of the containers is caught by the rotatable holder 13. The first gate 21 of the barrier 20 is opened when the rotatable holder 13 holding the container is rotated and inserted into the first delivering device 311 of the filling station 31 of the working space 30. During the collecting, the container is placed at the first delivering device 311, and a cap of the container is opened by the open-close device 312; the first delivering device 311 pivots back and forth to pour medium from the container to the collecting station 33; the container is filled by the filling mechanism 313, and then the cap of the container is closed by the open-close device 312. After the collecting, the container is caught by the rotatable holder 13 back to the container shelf 11.

The processes facilitated by the cell culture apparatus as described may be performed individually or in combinations.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A cell culture apparatus, comprising:
at least one storage space comprising
a container shelf mounted in the at least one storage space;
an upright track which is adjacent to the container shelf; and
a rotatable holder rotatably and moveably connected to the upright track;
at least one barrier which is adjacent to the upright track of the at least one storage space, each of the at least one barrier comprising a first gate; and
a working space having two opposite sides, comprising
a filling station comprising
a first delivering device having two opposite sides, and the first delivering device moveably mounted in the working space with one of the sides of the first delivering device nearby the at least one barrier;
an open-close device mounted in the working space nearby the other side of the first delivering device;
a filling mechanism which is adjacent to the open-close device and nearby the first delivering device; and
an inspecting station comprising
a first inspecting mechanism mounted in the working space, and the first inspecting mechanism being adjacent to the open-close device of the filling station; and
a second delivering device connected to the first inspecting mechanism.

2. The cell culture apparatus according to claim 1, wherein the at least one storage space further comprises a light tube mounted in the storage space.

3. The cell culture apparatus according to claim 1, wherein the working space further comprises a collecting station mounted beside the filling station.

4. The cell culture apparatus according to claim 1, wherein the second delivering device is a robotic arm.

5. The cell culture apparatus according to claim 1, wherein the inspecting station further comprises a second inspecting mechanism located between the first inspecting mechanism and the first delivering device.

6. The cell culture apparatus according to claim 1, wherein the cell culture apparatus further comprises
   a sterilization space connected to one of the sides of the working space, and the other side of the working space connected to the at least one barrier; and
   a control space which is adjacent to the storage space and the working space.

7. The cell culture apparatus according to claim 6, wherein the sterilization space comprises
   a second gate which is adjacent to the filling station of the working space; and
   a UV sterilizer mounted in the sterilization space.

8. The cell culture apparatus according to claim 6, wherein the sterilization space is a laminar flow hood.

9. The cell culture apparatus according to claim 1, wherein the at least one storage space is three storage spaces which are adjacent to one another.

10. A method of using a cell culture apparatus as claimed in claim 1, comprising the following steps:
    setting multiple containers into the container shelf;
    capturing one of the containers by the rotatable holder;
    opening the first gate of the barrier when the rotatable holder holding the container is rotated and inserted into the first delivering device of the filling station of the working space;
    processing the container by at least one of the following processes: a filling process, an inspecting process, and a collecting process;
    after processing the at least one process, placing the container at the first delivering device, and opening a cap of the container by the open-close device; filing the container by the filling mechanism, and then closing the cap of the container by the open-close device; and
    moving the container by the rotatable holder back to the container shelf.

11. The method of using a cell culture apparatus according to claim 10, wherein the method further comprises replacing the storage space or increasing an amount of the storage space when the storage space is culturing cells.

12. The method of using a cell culture apparatus according to claim 10, wherein the at least one process is the filling process, the container is placed at the first delivering device, and the cap of the container is opened by the open-close device; the container is filled by the filling mechanism, and then the cap of the container is closed by the open-close device.

13. The method of using a cell culture apparatus as claimed in claim 10, wherein the at least one process is the inspecting process, the container is placed at the first delivering device, and the second delivering device of the inspecting station delivers the container to the first inspecting mechanism.

14. The method of using a cell culture apparatus according to claim 13, wherein the method further comprises placing the container at the first delivering device, and delivering the container to the second inspecting mechanism and then to the first inspecting mechanism by the second delivering device of the inspecting station.

15. The method of using a cell culture apparatus as claimed in claim 10, wherein the at least one process is the collecting process, the container is placed at the first delivering device, and the cap of the container is opened by the open-close device; the first delivering device pivots back and forth to pour medium from the container to the collecting station; the container is filled by the filling mechanism, and then the cap of the container is closed by the open-close device.

* * * * *